United States Patent [19]
Venkatram et al.

[11] Patent Number: 5,302,771
[45] Date of Patent: Apr. 12, 1994

[54] PROCESS FOR UPGRADING THE QUALITY OF LIGHT ENDS

[75] Inventors: Ramdas Venkatram, Morris Township, Morris County; George E. Milliman, Fanwood, both of N.J.

[73] Assignee: Exxon Chemical Patents, Inc., Linden, N.J.

[21] Appl. No.: 15,269

[22] Filed: Feb. 8, 1993

Related U.S. Application Data

[63] Continuation of Ser. No. 833,615, Feb. 13, 1992, abandoned, which is a continuation of Ser. No. 682,040, Apr. 8, 1991, abandoned.

[51] Int. Cl.$^5$ .......................... C07C 7/12; C07C 7/00
[52] U.S. Cl. .................... 585/823; 585/824; 585/852; 585/854
[58] Field of Search ............ 585/823, 824, 852, 854

[56] References Cited

U.S. PATENT DOCUMENTS

| | | | |
|---|---|---|---|
| 3,141,729 | 7/1964 | Clarke et al. | 23/4 |
| 3,789,581 | 2/1974 | Carr et al. | 55/74 |
| 3,865,924 | 2/1975 | Gidaspow et al. | 423/230 |
| 4,433,981 | 2/1984 | Slaugh et al. | 55/59 |
| 4,493,715 | 1/1985 | Hogan et al. | 55/68 |
| 4,614,729 | 10/1986 | Crawford et al. | 502/401 |
| 4,717,785 | 1/1988 | Paxson | 585/823 |
| 4,795,545 | 1/1989 | Schmidt | 585/823 |
| 4,798,711 | 1/1989 | Neal et al. | 423/239 |
| 4,835,338 | 5/1989 | Lin | 585/824 |
| 4,877,920 | 10/1989 | Lush et al. | 585/823 |

FOREIGN PATENT DOCUMENTS

| | | |
|---|---|---|
| 901355 | 6/1985 | Belgium . |
| 0379394 | 7/1990 | European Pat. Off. . |
| 1383611 | 2/1975 | United Kingdom . |
| 2037805 | 7/1990 | United Kingdom . |

OTHER PUBLICATIONS

Katalco 59-3, Product bulletin KAT-59-3-1, and advertising literature designated CL-211-1 (1988), (page unavailable).

*Primary Examiner*—Anthony McFarlane
*Assistant Examiner*—Nhat D. Phan
*Attorney, Agent, or Firm*—Linda K. Russell

[57] ABSTRACT

The present invention is directed to a process for removing impurities from hydrocarbon streams, preferably light ends, such as propylene and ethylene, which is preferably in the liquid phase, by contacting the hydrocarbon stream containing an initial amount of an impurity with a chemical adsorbent which is composed of a modified alumina having a surface area within the range of about 10 m$^2$/g to about 300 m$^2$/g and a pore volume within the range of about 0.1 mL/g to about 1 mL/g under contacting conditions effective to result in a purified hydrocarbon stream containing a reduced amount of impurities, i.e., less than about 0.5% relative to the initial amount of the acid impurity present in the hydrocarbon stream, and more preferably within the 10 ppb range.

20 Claims, 5 Drawing Sheets

PROCESS FOR UPGRADING THE QUALITY OF LIGHT ENDS

This is a continuation of application Ser. No. 07/833,615, filed Feb. 13, 1992, and abandoned, which is a continuation of application Ser. No. 07/682,040, filed Apr. 8, 1991, now abandoned.

FIELD OF THE INVENTION

The present invention relates to processes for removing impurities from hydrocarbon streams. More particularly, the present invention is directed to removing impurities from hydrocarbon streams by contacting the hydrocarbon stream with a chemical adsorbent including a modified alumina having a surface area within the range of about 10 m$^2$/g to about 300 m$^2$/g and a pore volume within the range of about 0.1 mL/g to about 1 mL/g so as to result in a purified hydrocarbon stream containing a reduced amount of the impurities.

Specifically, the present invention is directed to removing impurities, such as $AsH_3$, $Ph_3CO_2$, COS, $H_2S$, from light ends, such as propylene, by contacting the propylene containing an initial amount of such an impurity with a chemical adsorbent comprising a modified alumina having a surface area within a range of about 10 m$^2$/g to about 300 m$^2$/g a pore volume within the range of about 0.1 mL/g to about 1 mL/g under contacting conditions effective to result in a purified propylene stream containing a reduced amount of such impurities.

DISCUSSION OF BACKGROUND AND MATERIAL INFORMATION

Impurities present in hydrocarbon streams, and particularly from light ends, such as propylene, pose various problems including contamination and of downstream processes, such as propylene polymerization adversely impacting catalyst utilization efficiency and product quality.

Conventionally, methods have been proposed to remove certain impurities, such as carbon dioxide, from gaseous streams which involve the use of liquids, such as solutions containing ethanolamine, ammonia, soda, carbonates and lyes, are ineffective in reducing the impurities to the extremely low levels required for the latest generation of highly selective catalysts in the downstream processes, such as propylene polymerization.

U.S. Pat. No. 3,141,729 discloses another approach which involves the use of solid adsorbent materials, such as molecular sieves, calcium oxide, finely-divided micro-porous silver oxide dispersed in an admixture with aluminum oxide, and supported cogels of divalent and trivalent metals for such purpose.

U.S. Pat. No. 3,865,924 discloses the use of a synergistic mixture of carbonate and alumina for similar purposes, but requires the addition of water since the adsorption reaction is:

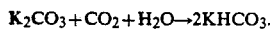

$$K_2CO_3 + CO_2 + H_2O \rightarrow 2KHCO_3.$$

U.S. Pat. No. 4,433,981, SLAUGH et al., is directed to the removal of carbon dioxide from a gaseous stream by contacting the stream with an adsorbent prepared by impregnating a porous alumina with an alkali metal or alkaline earth metal oxide or salt decomposable upon calcination, and subsequently calcining the impregnated alumina at about 350° C. -700° C.

In general, alumina is a known adsorbent in many chemical processes, such as the polymerization of olefins, such as ethylene, for the removal of water and small concentrations of methanol, carbonyl-containing compounds and peroxides. However, the use of alumina has certain disadvantages which adversely affect its use as an adsorbent. Among such disadvantages is that alumina is not always effective as an adsorbent for the removal of, for example, $CO_2$, from gaseous olefin-containing streams which contain $CO_2$ at low level concentrations, for example, down to 1 ppm.

Molecular sieves have been used as adsorbents for $CO_2$, but in some instances have been found to be inefficient when used for the removal of $CO_2$ from a gaseous stream containing low molecular weight olefins, such as ethylene.

Caustic scrubbers, or bulk caustic scrubbers, have been proposed for use as adsorbents for $CO_2$ from a gaseous stream, but suffer certain disadvantages, including posing safety problems and adding water to the stream.

U.S. Pat. No. 4,493,715 is directed to a process for the removal of $CO_2$ from a gaseous stream containing at least one $C_2$ to $C_4$ olefin which involves contacting the stream with a regenerable calcined alkali metal compound-treated alumina.

U.S. Pat. No. 4,614,729, STAUFFER CHEMICAL COMPANY, discloses the removal of catalyst poisons, such as $CO_2$, CO, COS, $H_2O$, $H_2S$, $O_2$, and acetylenes from hydrocarbon fluids, such as liquified $C_2$-$C_{30}$ alkenes. The catalyst used for this purpose is alumina treated with an organometallic compounds from Groups II, III and IV.

British Patent No. GB 1,383,611, FARBEWERKE HOECHST, discloses the removal of impurities at levels below 10 ppm from propylene by treating compressed propylene with mineral adsorbents, such as alumina, which may also contain other oxides, such as $Na_2O$.

Belgium Patent No. BE 901,355, LABOFINA, is directed to the removal of low level impurities by passing the propylene over alumina treated with trialkyl aluminum. The purified propylene is disclosed as containing less than 30 ppm COS.

U.S. Pat. No. 4,798,711, NOXSO CORP., describes a process for removing nitrogen oxides and/or sulfur oxides from a gas by using an alkali metal-alumina sorbent.

Katalco 59-3 has been disclosed as a dechlorination catalyst which is specially formulated for the removal of chlorides in advertising publications, i.e., product bulletin KAT-59-3-1. As described Katalco 59-3 is to be used principally for the removal of reactive chlorides from natural gases and other hydrocarbon streams by absorption; for the removal of organic chlorides following hydrogenation over a hydro-treating catalyst; and the dehalogenation of combined chloride/fluoride hydrocarbon streams. Katalco 59-3 is disclosed as having a high chloride capacity, and reduces the chloride content of gas streams to below the normal detection level. It is also disclosed as being compatible with liquid hydrocarbons and operates over a wide range of process conditions. As advertised in advertising literature designated CL-211-1, Katalco 59-3 is described as a solid chemical adsorbent for the removal of chlorides from gas streams. It is also disclosed as being useful to purify any dry process stream where there is a need to prevent corrosion or filing of downstream equipment or deactivation of process catalysts.

SUMMARY OF THE INVENTION

Notwithstanding the previously-described efforts, catalysts used in the manufacture of polypropylene are extremely sensitive to impurities in the propylene feedstock such as $CO_2$, COS, $H_2S$, $H_2O$ and the like, such as arsine, phosphine, and the like. In an attempt to solve the problems associated with catalyst deactivation as a consequence of the presence of such impurities in the propylene feedstock there is a continuing concern to achieve lower and lower levels of these impurities in the propylene feedstock.

Accordingly, the present invention is based on the discovery of a process wherein impurities in the propylene stream can be reduced to extremely low levels, such as $H_2S$ in the range of 100 wppb, $CO_2$ in the range of 1 wppm by passing the propylene stream through a bed of reagent or chemical adsorbent in accordance with the present invention.

In accordance with the present invention, a reagent, also referred to herein as a chemical adsorbent has been discovered which is unexpectedly effective in removing impurities, such as $CO_2$, COS, $H_2S$, $ASH_3$ and $H_2O$, and the like from light ends, such as propylene.

The reagent or chemical adsorbent suitable for purposes of the present invention i.e., removing the previously identified impurities, is impregnated sodium on alumina. The chemical adsorbent which is particularly suitable for purposes of the present invention preferably has a surface area of about 60 $m^2/g$ and a pore volume of about 0.3 mL/g, and more preferably also has a bulk density within the range of about 40 lb./$ft^3$ to about 60 lb./$ft^3$. More preferably, the chemical adsorbent in accordance with the present invention is spherical modified alumina having the previously-described characteristics, which preferably have a size within the range of about 1/16" diameter to about 3/16" diameter. The modified alumina chemical adsorbent preferred for purposes of the present invention is impregnated with a metallic substance selected from the group consisting of lithium, potassium, sodium, calcium, magnesium and barium; and the alumina is selected from the group of sources of alumina consisting of alpha alumina and gamma alumina. Most preferably the chemical adsorbent is a modified alumina having a surface area of about 60 $m^2/g$, a pore volume of 0.3 mL/g and a bulk density of 55 lb./$ft^3$ in spherical form having a size within the range of about 1/16" diameter to about 3/16" diameter, and is commercially available from Katalco Corporation as Katalco 59-3.

The present invention is also directed to a process for removing impurities from hydrocarbon streams which involves contacting the hydrocarbon stream containing an initial amount of an impurity with a chemical adsorbent, as described above, under contacting conditions effective to result in a purified hydrocarbon stream containing a reduced amount of the impurities.

In accordance with the present invention, the impurities which may be removed are selected from the group consisting of $CO_2$, COS, $H_2S$, $H_2O$, $AsH_3$ and $PH_3$, as well as from the group consisting of COS, $H_2S$, $H_2O$, $AsH_3$ and $PH_3$.

In accordance with the present invention, an impurity present in the hydrocarbon stream, e.g. $CO_2$, may be reduced to less than about 1.5% based on the initial amount of the impurity in the hydrocarbon feed stream.

The chemical absorption process of the present invention is performed at contacting conditions which include temperatures within the range of about 10° F. to about 150° F., and preferably within the range of 30° F. to about 120° F.; and pressures within the range of about 50 psig to about 500 psig, and preferably pressures within the range of about 150 psig to about 350 psig; and space velocities within the range of about 0.1 VHSV to about 25 VHSV, and preferably within the range of about 0.5 VHSV to about 1 VHSV.

The process of the present invention is preferably performed to remove impurities from hydrocarbon streams in the liquid phase, preferably wherein the hydrocarbon streams include a member selected from the group consisting of olefins, saturated hydrocarbons and mixture thereof. More preferably the light end olefins may be selected from the group of $C_2$ olefins and saturated hydrocarbons, $C_3$ olefins and saturated hydrocarbons, $C_4$ olefins and saturated hydrocarbons, and mixtures of $C_2$ to $C_4$ olefins and saturated hydrocarbons. Most preferably, however, the light ends are selected from the group consisting of ethane, propane, butanes, ethylene, and propylene, and most preferably propylene.

In accordance with the present invention, the modified alumina chemical adsorbent is loaded in adsorbent beds located downstream from conventional alumina driers or in lieu of such conventional alumina driers.

DETAILED DESCRIPTION

Figure 1:
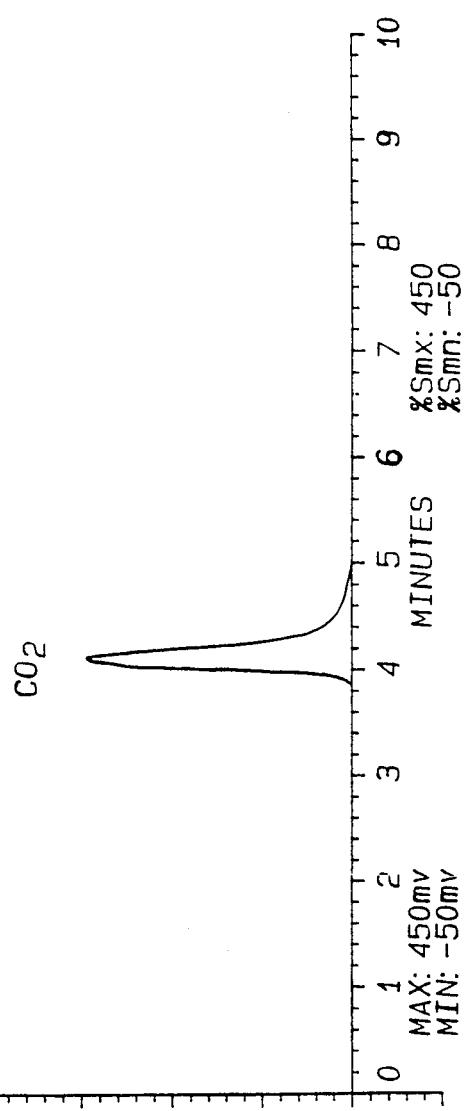
FIG. 1 is a graph illustrating the experimental data generated in Example 1 discussed below.

Impurities, including $CO_2$, COS, $H_2S$, $H_2O$, $AsH_3$ and $PH_3$, are effectively removed from hydrocarbon streams, such as liquid olefin streams, using the chemical adsorbents in accordance with the present invention.

In accordance with the present invention, certain chemical adsorbents, have unexpectedly been discovered to be particular effective for the removal of impurities from liquid hydrocarbon streams, such as olefins, for example, propylenes, and are particularly effective for the removal of such impurities from propylene streams.

The chemical adsorbent most preferred for purposes of the present invention is a modified alumina having a surface area within the range of about 10 $m^2/g$ to about 300 $m^2/g$ and a pore volume within the range of about 0.1 mL/g to about 1 mL/g, and more preferably also having a surface area within the range of about 60 $m^2/g$ and a pore volume of about 0.3 mL/g, as well as a bulk density within the range of about 40 lb./$ft^3$ to about 60 lb./$ft^3$, most preferably wherein the bulk density is about 55 lb./ft.$^3$, wherein the modified alumina is spherical having a size within the range of about 1/16" diameter to about 3/16" diameter, and is prepared, for example, by impregnating or providing an alumina with a metal selected from the group consisting of lithium, potassium, calcium, magnesium, barium and sodium.

The most preferred adsorbent for purpose of the present invention is a solid chemical adsorbent commercially marketed as Katalco 59-3 by Katalco, a business unit of ICI Americas, Inc.

In accordance with the present invention, such chemical adsorbents have been found to be extremely effective in removing relatively small amounts of such impurities to produce a propylene stream which is essentially devoid of such impurities, i.e., which are present in the resultant purified hydrocarbon stream at less than about 1.5%, and more preferably less than about 10 ppb.

This is particularly unexpected inasmuch as Katalco 59-3 has been disclosed as a dechlorination catalyst which is specially formulated for the removal of chlorides in advertising publications. In this regard, Katalco 59-3 has been described as being used principally for: the removal of reactive chlorides from natural gases and other hydrocarbon streams by absorption; for the removal of organic chlorides following hydrogenation over a hydro-treating catalyst; and the dehalogenation of combined chloride/fluoride hydrocarbon streams. Katalco 59-3 is disclosed as having a high chloride capacity, and reduces the chloride content of gas streams to below the normal detection level. Katalco 59-3 is further described as a solid chemical adsorbent for the removal of chlorides from gas streams. It is also disclosed as being useful to purify any dry process stream where there is a need to prevent corrosion or filing of downstream equipment or deactivation of process catalysts. Katalco 59-3 has also been disclosed as being useful to purify catalytic reformer offgases containing ammonium chloride and HCl so as to prevent fouling problems associated with these chlorides. Katalco 59-3 is described as a high capacity adsorbent exhibiting 5-6 times higher absorptive capacity than alternative products, such as activated alumina; in this regard, Katalco 59-3 is disclosed as absorbing up to 8.5 lb. of chloride per ft.$^3$. Katalco 59-3 has been described as having a unique pore structure and chemically-active surface area which provides rapid chloride pickup, chloride absorption close to 100% theoretical in the saturated zone, and no chloride slip. Notwithstanding such disclosures, it is not believed that, prior to the present invention, KATALCO 59-3 was used in a manner disclosed and claimed herein for purposes of the present invention.

Suitable impregnating metal compounds for purposes of the present invention include lithium, potassium, sodium, calcium, magnesium, and barium.

Figure 4:
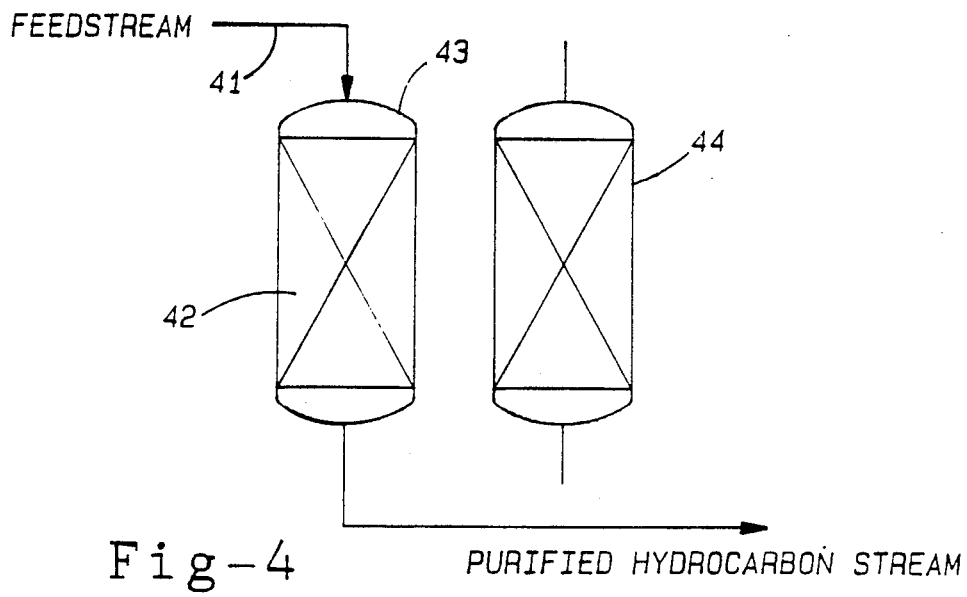
FIG. 4 is a flow diagram of the process for upgrading the quality of light ends in accordance with the present invention.

The process for removing impurities from hydrocarbon streams using the chemical adsorbent in accordance with the present invention, referring to FIG. 4, involves contacting the hydrocarbon stream 41 containing saturated hydrocarbons and/or olefins, including an initial amount of an impurity with the chemical adsorbent 42 under contacting conditions effective to result in a purified olefin stream containing a reduced amount of the impurity. The chemical adsorbent is preferably contained in an adsorbent bed 43, zone or other suitable vessel and the hydrocarbon stream, preferably containing olefins, is fed to the chemical adsorbent bed under conditions suitable for the adsorbent bed and process system. As shown in FIG. 4, the hydrocarbon stream 41 containing the impurities to be removed is contacted in a single stage with the chemical adsorbent 42 contained in adsorbent bed 43. Optionally, at least one other adsorbent bed 44, which is essentially the same in structure and adsorbent content, may be provided to alternate with adsorbent bed 43 if taken off-line. Suitable contacting conditions include a pressure within the range of about 50 to about 500 psig, and preferably 150-350 psig; temperatures within the range of about 10° F. to about 150° F., and preferably within the range of 30° F. to about 120° F.; and a space velocity within the range of about 0.1 to about 25 VHSV and preferably within the range of about 1 to about 15 VHSV. The olefin stream, most preferably in the liquid phase, is fed to the chemical adsorbent bed at about 5 VHSV at a temperature of about 60° F. under a pressure of 300 psig.

Figure 5:
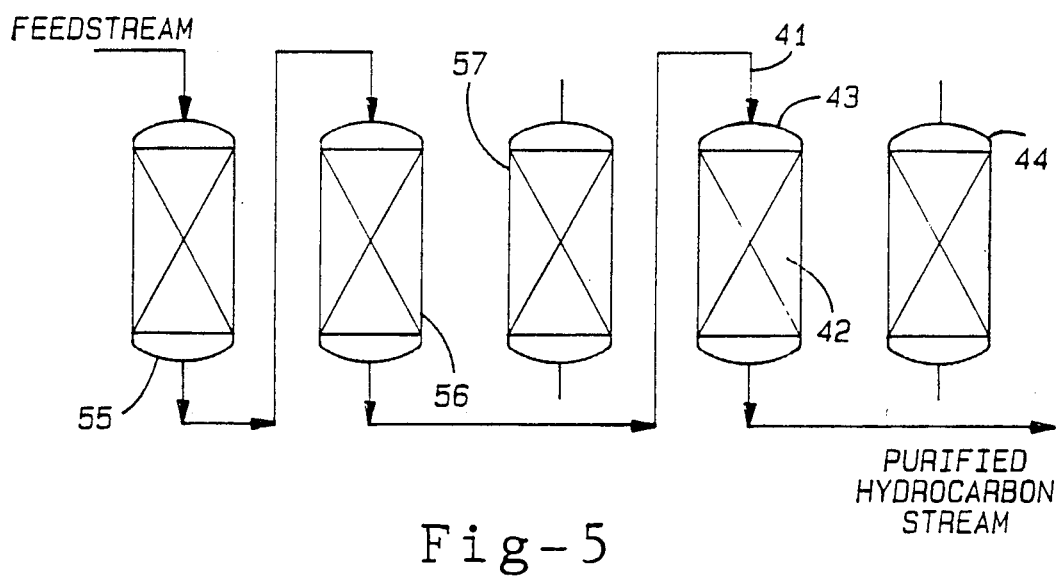
FIG. 5 is a flow diagram of the process of the present invention wherein the modified alumina adsorbent is loaded in adsorbent beds located downstream from alumina driers.

Referring now to FIG. 5, a process for removing impurities using the chemical adsorbent in accordance with the present invention is shown in a flow diagram which illustrates an embodiment where the modified alumina adsorbent 42 is loaded in adsorbent beds 43,44 located downstream from at least one alumina drier, but preferably two alumina driers 55, 56. Optionally, a spare alumina drier 57 may be provided to alternate with either or both of alumina driers 55,56 if one or both is/are taken off-line.

Although for purposes of the present invention the examples have been conducted using the olefin in the gaseous phase, it is believed that the reagent would be equally or more effective, when the hydrocarbon stream is a liquid rather than a gas. Moreover although the present invention has been described for treating an olefin stream, such as propylene, feeds such as ethylene may also be treated in accordance with the present invention, for the reason that, as shown in the examples, the reagent is effective in removing impurities from gaseous streams such as Helium and Propylene. As indicated above, the reagent is expected to be equally effective, if not more, for removal of these impurities from liquid hydrocarbon streams. The reagent, therefore, is suitable for removing impurities from both liquid and gaseous hydrocarbon streams.

Therefore, in general, the process of the present invention may be carried out at a temperature of about 10° F. to about 150° F. The preferred temperatures which have been used for purposes of the present invention are within the range of about 30° F. to about 120° F.

Similarly, pressures under which the chemical adsorption process of the present invention may be practiced will be from about 50 psig to about 500 psig. The pressures which have been used and are preferred for purposes of the present invention fall within the range of about 150 psig to about 350 psig.

The following is a detailed description of the chemical absorption process in accordance with the present invention wherein a propylene stream containing impurities was contacted with the chemical adsorbent comprising a modified alumina in accordance with the present invention, so as to reduce the initial amount of the impurities.

The light ends stream processed was polymer grade propylene. The normal analysis of the stream is as follows: Propylene: >99.5%; Propane: <0.5%; $CO_2$: <2 wppm; COS: <1 wppm; $AsH_3$: <200 wppb; $H_2O$: <10 wppm. Experiments conducted with $CO_2$ and $H_2S$ (in Helium carrier gas) have shown that the Katalco reagent would almost quantitatively remove these impurities i.e. to below detectable levels using current measuring techniques. A significant amount of COS and $AsH_3$, are also removed by Katalco 59-3.

The purified hydrocarbon stream, i.e., light ends, and most preferably propylene, which has a substantially reduced amount of impurities may then be processed, for example, in polymerization processes to produce polypropylene wherein the polymerization catalysts, which are otherwise extremely sensitive to the impurities which would otherwise be present in the propylene feedstock, remain active for substantially longer periods of time than if the propylene stream was not treated in accordance with the present invention.

Figure 6:
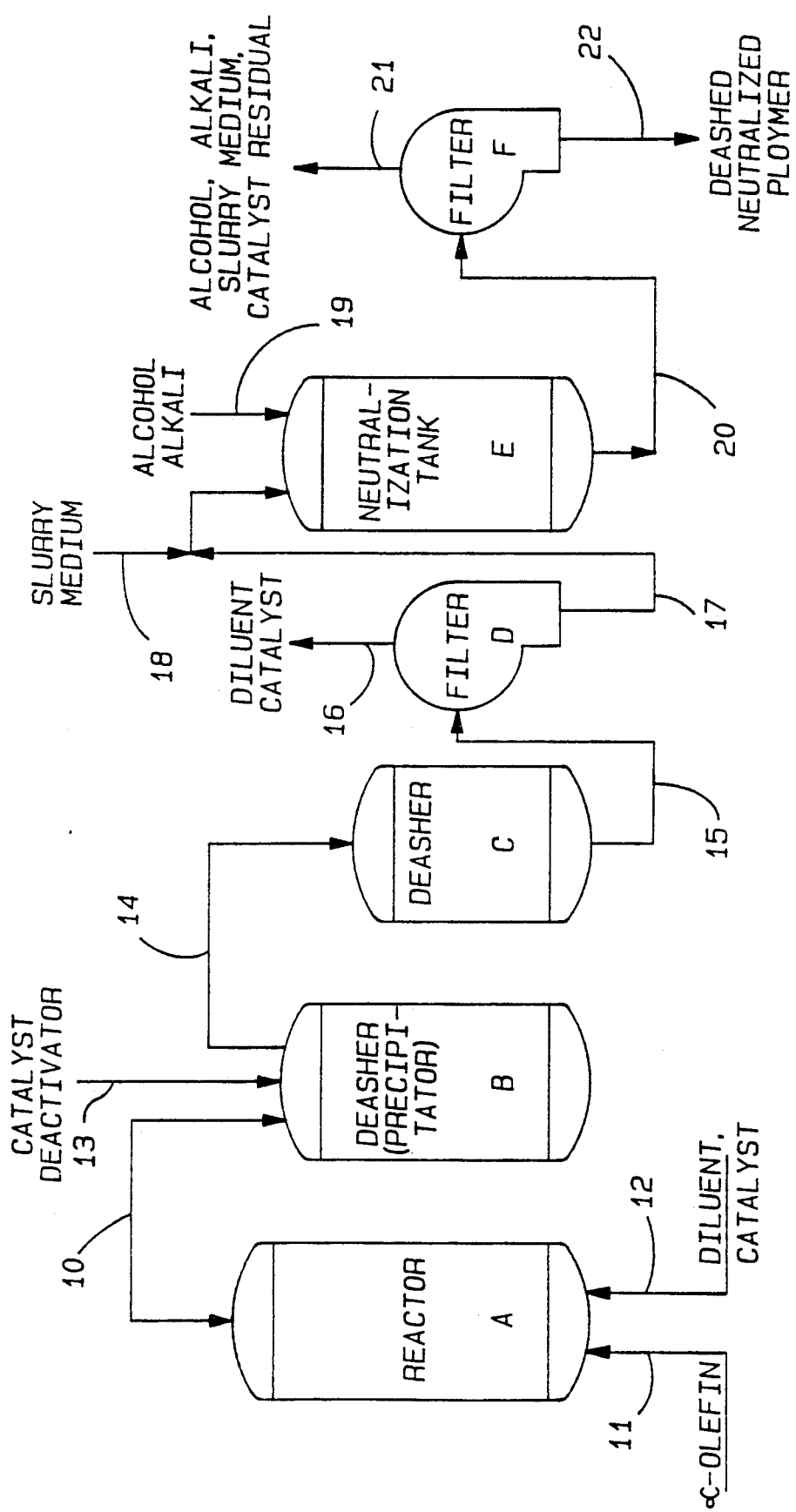
FIG. 6 is a flow diagram of a propylene process, wherein propylene, treated in accordance with the present invention, is used as a feedstock.

Reference is made to FIG. 6 in which schematically illustrate a propylene process wherein propylene, purified in accordance with the present invention is used as a feedstock. The attached diagram are schematics of the representative processes which may be used for polypropylene manufacture.

In FIG. 6 a particular environment embodying the present invention is depicted. In FIG. 6 a continuous process is shown, although the present invention is equally applicable to batch type operations. A stream of high purity propylene is fed through line 11 into a reactor A where it is agitated with a diluent, added through line 12, such as xylene with a Ziegler catalyst comprising 3/1 $TiCl_3/AlCl_3$ and diethyl aluminum chloride in the diluent. The reaction product is carried to precipitator B via line 10 where a catalyst deactivator such as methanol is introduced through line 13 and agitated with reaction product to deactivate the catalyst. The mixture from precipitator B passes the deasher C via line 14 where the contacting is continued and hence to filter D through line 15. In filter D the solvent and a substantial portion of the catalyst are removed through line 16 while the filter cake is reslurried with xylene and passed by line 17 into the neutralization tank E. The neutralizing solution of the present invention, i.e., the alcohol and alkali solution, methanol and Na methylate, enter tank E through line 19 and are agitated with the slurried polymer particles which then pass through line 20 to filter F. The xylene, methanol Na methylate and further catalyst residuals are removed as filtrate through line 21 and the deashed, neutralized polypropylene comes out as a moist powder, which may be water washed (not shown) and subsequent dried (not shown).

EXAMPLES

The following examples are given to illustrate the advantages of the present invention, but are not intended, nor should they be construed, to limit the scope of the invention to the specifics which are recited therein for this purpose.

Example 1

A lab test was conducted to determine the efficiency of the chemical adsorbent of the present invention. Helium, containing a 100 vppm $CO_2$ in helium, was passed through a cylindrical plastic tube, 125 mm in length and 17 mm in diameter with a bulbous end being 30 mm in diameter containing approximately 32 grams of Katalco 59-3 chemical adsorbent composed of a modified alumina, in spherical form, having a diameter within the range of about $\frac{1}{8}"$ to about 3/16", a surface area of about 60 $m^2/g$, a pore volume of about 0.3 mL/g, and a bulk density of about 55 $lb./ft.^3$. The $CO_2$ content of the feed, i.e. helium, and the effluent was determined using a gas chromatographic analytical system that included a methanator followed by a Flame Ionization Detector commonly used in the industry. It was found that the effluent contained ca.1 vppm of $CO_2$.

Figure 2:
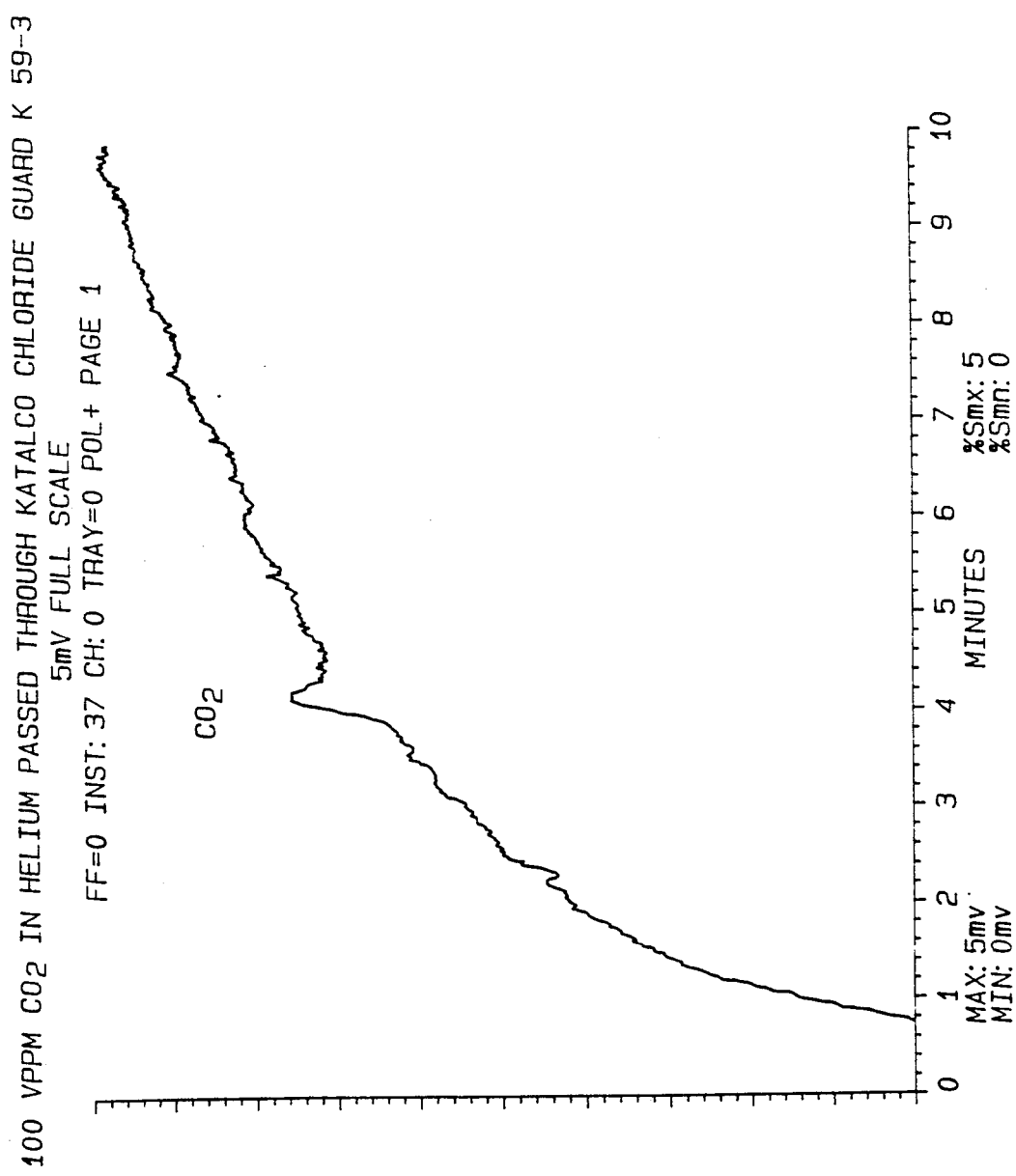
FIG. 2 is another graph of experimental data generated in Example 1.
Figure 3:
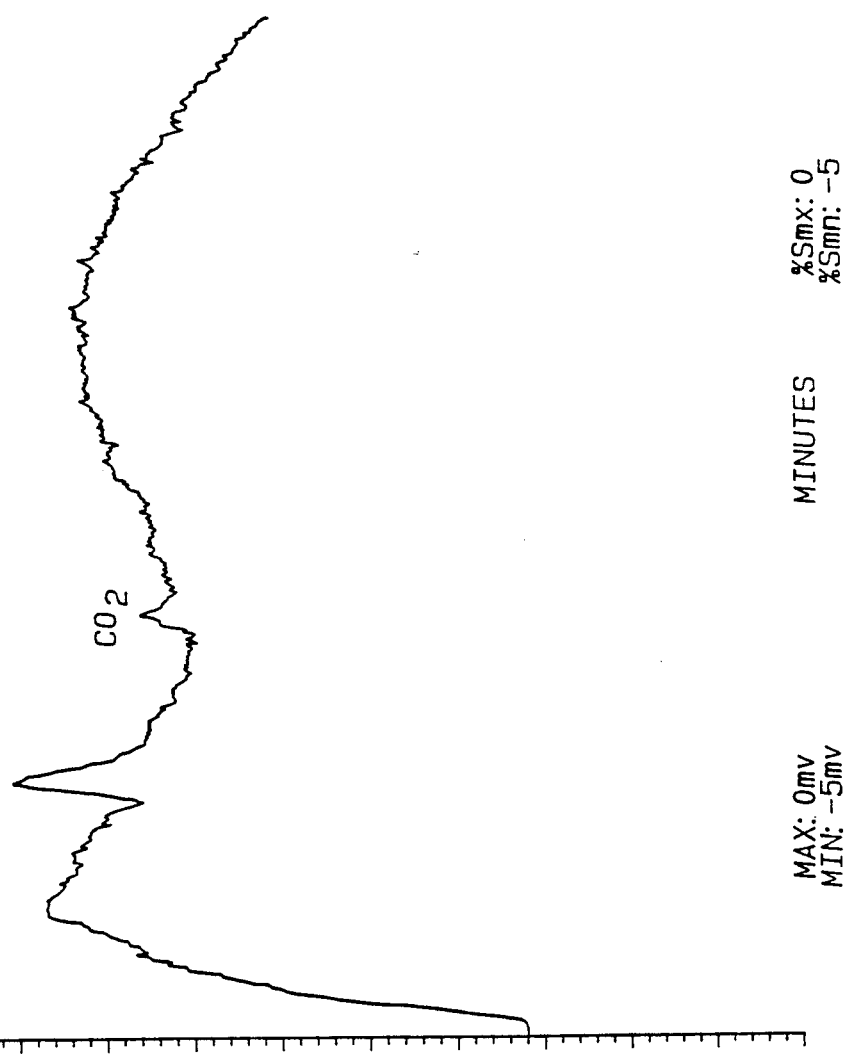
FIG. 3 is another graph of experimental data generated in Example 1.

As shown in the attached FIGS. 1-3, the chemical adsorbent used in accordance with the present invention removed greater than 99.5% of the $CO_2$ in the He feed, wherein $CO_2$ in the feed was 145 mv signal; and the $CO_2$ in the effluent was 0.7 mv signal.

In accordance with the present invention, it has been discovered that the process for removing impurities from light ends using the chemical adsorbent in accordance with the present invention is valuable in basic as well as retrofit applications, particularly in high purity olefin manufacturing plants, such as propylene, ethylene and the like.

The high capacity and the sharp breakthrough curve, as illustrated in the attached figures, indicate that the chemical adsorbent used in accordance with the present invention improves the consistency of product quality even during upsets in the process upstream, thereby leading to an increase in impurity levels. Typical treatment techniques used for lowering impurity levels in propylene include absorption processes using an organic amine and/or caustic solutions followed by fractionation and drying used alumina driers.

However, such a system has a few disadvantages. In this regard, the impurities, such as $CO_2$, $H_2S$, and the like, are not lowered to "undetectable" levels. Also, in case of upsets in the absorption processed upstream, the impurity levels increase substantially and are beyond the capacity of the downstream processes to handle, thereby throwing the propylene product quality "off-spec".

In contrast, use of Katalco 59-3 in an adsorbent bed either "downstream of" or "in lieu of" the alumina driers offers several advantages. In accordance with the present invention, such use of Katalco 59-3 has been discovered to improve propylene quality by reducing certain trace impurities, such as $CO_2$ and $H_2S$, to extremely low levels. Also, it has been discovered that Katalco 59-3 has a significantly higher capacity to handle the higher impurity levels resulting from upsets in the upstream absorption processes, thereby contributing a significantly to the product quality assurance process.

In a typical high purity propylene operation embodying the process for removing impurities from hydrocarbon streams using the chemical adsorbent in accordance with the present invention, the chemical adsorbent can be loaded in adsorbent beds downstream from an alumina drier, or alternatively in lieu of them.

Example 2

A gas consisting of 9.2 vppm $H_2S$ in helium was passed through the same tube as in Example 1 containing a new charge of Katalco 59-3. The $H_2S$ content of the feed and effluent was measured using a Tracor-Atlas Total Sulfur Analyzer. No detectable $H_2S$ was found in the effluent, i.e., <0.1 vppm.

Example 3

Also, a gas consisting of 10.3 vppm COS in helium was passed through the same tube and Katalco 59-3 used in Experiment 2. The COS content of the feed and effluent was measured using a Tracor-Atlas Total Sulfur Analyzer. This experiment was performed on two separate days. On Day 1 the effluent was found to contain 4.3 vppm of COS and on Day 2 the effluent was found to contain 1.8 vppm COS.

Example 4

Also, a sample of high purity propylene was vaporized and passed through the same tube and Katalco 59-3 used in Experiment 3. The $AsH_3$ content of the feed and effluent was measured using an MDA Arsine Analyzer. The feed was found to contain 31 wppb $AsH_3$ and the effluent was found to contain 13 wppb $AsH_3$.

Although the invention has been described with reference to particular means, materials and embodiments, from the foregoing one skilled in the art can easily ascertain the essential characteristics of the present invention; and various changes and modifications may be made to various usages and conditions without departing from the spirit and scope of the invention as described in the claims that follow.

What is claimed is:

1. A process for removing impurities from hydrocarbon streams, said process comprising:
    contacting a hydrocarbon stream containing an initial amount of at least one impurity selected from the group consisting of $AsH_3$ and $PH_3$ with a chemical adsorbent comprising a modified alumina impregnated with a metal selected from the group consisting of lithium, sodium, potassium, calcium, magnesium, and barium, and having a surface area within the range of about 10 $m^2/g$ to about 300 $m^2/g$ and a pore volume within the range of about 0.1 mL/g to about 1 mL/g under contacting conditions effective to result in a purified hydrocarbon stream containing a reduced amount of said impurity.

2. The process as defined by claim 1, wherein said reduced amount of impurity is less than about 1.5% of said initial amount of said impurity.

3. The process as defined by claim 1, wherein said modified alumina comprises a surface area of about 60 $m^2/g$ and a pore volume of about 0.3 mL/g.

4. The process as defined by claim 3, wherein said modified alumina has a bulk density within the range of about 40 lb./$ft.^3$ to about 60 lb./$ft.^3$.

5. The process as defined by claim 4, wherein bulk density is about 55 lb./$ft.^3$.

6. The process as defined by claim 5, wherein said modified alumina is spherical.

7. The process as defined by claim 6, wherein said modified alumina has a size within the range of about 1/16" diameter to about ⅜" diameter.

8. The process defined by claim 1, wherein said modified alumina comprises alumina selected from the group consisting of alpha alumina and gamma alumina.

9. The process as defined by claim 8, wherein said contacting conditions comprise a pressure within the range of about 50 psig to about 500 psig.

10. The process as defined by claim 9, wherein said pressure is within the range of about 150 psig to about 350 psig.

11. The process as defined by claim 9, wherein said hydrocarbon stream is in the liquid phase.

12. The process as defined by claim 8, wherein said contacting conditions comprise a space velocity within the range of about 0.1 VHSV to about 25 VHSV.

13. The process as defined by claim 12, wherein said space velocity is within the range of about 0.5 VHSV to about 1 VHSV.

14. The process as defined by claim 1, wherein said contacting conditions comprise a temperature within the range of about 10° F. to about 150° F.

15. The process as defined by claim 14, wherein said temperature is within the range of about 30° F. to about 120° F.

16. The process as defined by claim 14, wherein said hydrocarbon stream comprises a member selected from the group of olefins and saturated hydrocarbons.

17. The process as defined by claim 16, wherein said olefins are light ends selected from the group olefins and saturates of $C_2$, $C_3$, $C_4$, and mixtures of $C_2$ to $C_4$.

18. The process as defined by claim 17, wherein said light ends are selected from the group ethane, butane, butylene, ethylene and propylene.

19. The process as defined by claim 18, wherein said light ends is propylene.

20. The process as defined by claim 19, wherein said modified alumina is loaded in adsorbent beds downstream from alumina driers.

* * * * *